United States Patent

Minagawa et al.

[11] 4,362,830
[45] Dec. 7, 1982

[54] HINDERED BIS-PHENOL PHENYL PHOSPHITES AND SYNTHETIC RESIN COMPOSITIONS HAVING ENHANCED STABILITY TO HEAT AND LIGHT

[75] Inventors: Motonobu Minagawa, Koshigaya; Yutaka Nakahara, Iwatsuki, both of Japan

[73] Assignee: Adeka Argus Chemical Co., Ltd., Urawa, Japan

[21] Appl. No.: 220,406

[22] Filed: Dec. 29, 1980

[30] Foreign Application Priority Data

Jan. 10, 1980 [JP] Japan .................................. 55-1542

[51] Int. Cl.$^3$ .................... C08K 5/52; C07D 251/34; C07D 69/90
[52] U.S. Cl. .................................. 524/101; 260/936; 260/927 R; 524/118; 544/214
[58] Field of Search ............... 260/45.85 B, 45.8 NT, 260/927 R, 936; 544/214, 221; 524/101, 118

[56] References Cited

U.S. PATENT DOCUMENTS

| | | | |
|---|---|---|---|
| 3,285,855 | 11/1966 | Dexter et al. | 260/45.85 B |
| 3,297,631 | 1/1967 | Bown et al. | 260/45.8 R |
| 3,658,743 | 4/1972 | Bevilacqua | 260/45.7 PH |
| 3,707,542 | 12/1972 | Steinberg et al. | 544/221 |
| 4,094,855 | 6/1978 | Spivack | 260/927 R |
| 4,196,117 | 4/1980 | Spivack | 260/45.8 R |
| 4,252,750 | 2/1981 | Buysch et al. | 260/927 R |
| 4,288,391 | 9/1981 | Spivack | 260/927 R |

*Primary Examiner*—V. P. Hoke

[57] ABSTRACT

Hindered bis-phenol phenyl phosphites are provided having the structure:

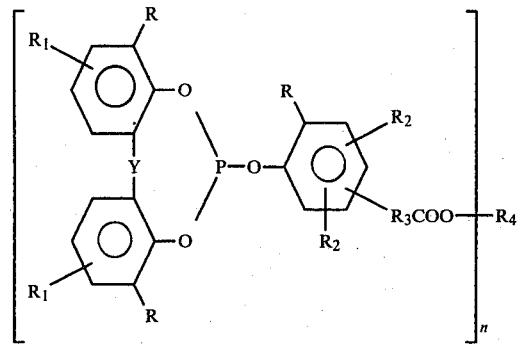

wherein:
R is selected from the group consisting of alkyl having from one up to about eighteen carbon atoms; cycloalkyl having from three up to about twelve carbon atoms; alkaryl and aryl having from six to about eighteen carbon atoms; preferably, a bulky group such as iso, secondary or tertiary alkyl having from three to about ten carbon atoms; or cycloalkyl having six to twelve carbon atoms;

$R_1$ and $R_2$ are each selected from the group consisting of hydrogen; alkyl having from one to about eighteen carbon atoms; cycloalkyl having from three up to about twelve carbon atoms; alkaryl and aryl having from six to about eighteen carbon atoms; and are preferably in a position ortho to a phenolic hydroxyl or phenoxy group, if available;

$R_3$ is alkylene having from one to about six carbon atoms;

$R_4$ is selected from the group consisting of alkylene, cycloalkylene, and aralkylene, the residue of a monohydric or polyhydric alcohol, having from one to about eighteen carbon atoms, and from none to three hydroxyl groups (originally one to four hydroxyl groups);

Y is selected from the group consisting of a direct carbon to carbon bond; thio sulfur —S—; oxy oxygen —O—; alkylidene having from one to about six carbon atoms; and cycloalkylidene having from four to about eight carbon atoms; and n is 1, 2, 3, or 4, according to the valence of $R_4$; as well as synthetic resin compositions having an enhanced resistance to deterioration by heat and/or light due to the presence of an organic phosphite of this class.

26 Claims, No Drawings

HINDERED BIS-PHENOL PHENYL PHOSPHITES AND SYNTHETIC RESIN COMPOSITIONS HAVING ENHANCED STABILITY TO HEAT AND LIGHT

Polypropylene and other polyolefins such as polyethylene, polybutylene and polyisopentylene show a strong tendency to deteriorate in physical properties at elevated temperatures and when exposed to ultraviolet light. The deterioration is evidenced by, among other things, a decrease in viscosity, a tendency to become brittle, and a discoloration which is particularly pronounced at the exposed edge of the material. This deterioration can be accompanied by distortion, cracking, and powdering of the material. The deterioration is accentuated in the presence of oxygen.

To overcome these difficulties, many stabilizer systems have been proposed for combination with polyolefins, with varying degrees of success. No single stabilizer has proved adequate, and combinations of stabilizers are consequently used almost exclusively. Most stabilized polyolefins on the market contain one or more of such stabilizer combinations. The deterioration appears to be due to a combination of factors, and a combination of stabilizers is therefore more capable of coping with the various types of deterioration. However, the retention of good physical properties over long periods of time remains rather difficult to achieve.

Of the many stabilizer systems that have been proposed, one particularly satisfactory stabilizer system is described in U.S. Pat. No. 3,255,136, patented June 7, 1966 to Arthur Hecker, Otto S. Kauder and Norman Perry. This stabilizer system comprises three stabilizers: an organic mono- or polyhydric phenol, an organic phosphite, and a thiodipropionic acid ester. An additional fourth ingredient, which is preferred but not essential, is a polyvalent metal salt of an organic acid. These three and four stabilizers together give an enhanced stabilization which is not obtainable from any of them alone, or in combinations of two.

In these combinations, the phenol alone gives an improved resistance to embrittlement and reduction in melt viscosity of polypropylene at elevated temperatures, but little assistance as to maintenance of color. The phosphite alone is a rather poor stabilizer in preventing deterioration in the first two properties, but it does assist in resisting discoloration. The two together are worse than the phenol alone in every respect except color, which is intermediate.

The thiodipropionic acid ester by itself only improves resistance to embrittlement. The polyvalent metal salt of an organic acid by itself only prevents discoloration. In combinations with the phenol, the color is worse than with the salt alone, and combinations with phosphite only, discoloration is prevented. The effectiveness of all three or four ingredients taken together against all of these types of deterioration is therefore particularly surprising.

The organic phosphite can be any organic phosphite having the formula $(RA)_3-P$, in which A can be oxygen or sulfur or a mixture of the same, and R is aryl, alkyl, cycloalkyl, aralkyl or aralkaryl in any combination. A variety of tris-alkaryl phosphites are disclosed, such as tris-(tertiary-octyl-phenyl)phosphite and tris-(tertiary-nonyl-phenyl)phosphite, but no tris-(alkaryl)phosphites having more than one alkyl group per phenyl group.

Organic phosphites have been widely used as stabilizers for polyolefins and similar polymeric materials, and many different types of phosphites, some of rather complex structure, have been proposed. U.S. Pat. Nos. 3,255,136 and 3,655,832 have suggested organic phosphite-phenol transesterification products, the preferred phenol being a bis-phenol. Other types of tris-(alkaryl)phosphite esters have been disclosed in U.S. Pat. Nos. 2,220,113; 2,220,845; 2,246,059; 2,419,354; 2,612,488; 2,732,365; 2,733,226; and 2,877,259. Additional tris-(alkaryl)phosphites are disclosed in U.S. Pat. Nos. 3,167,526 to Nicholson, patented Jan. 26, 1965; 3,061,583 to Huhn and Sheets, patented Oct. 30, 1962; 3,829,396 to Oakes and Cross, patented Aug. 13, 1974; French Pat. Nos. 1,496,563 to U.S. Rubber Company, délivré Aug. 21, 1967, and 1,497,390 to Ethyl Corporation, délivré Aug. 28, 1967; and British Pat. Nos. 1,058,977, published Feb. 15, 1967, to Hooker Chemical Corporation and 1,143,375, published Feb. 19, 1969, to Uniroyal Inc.

Oakes et al disclose bis-(2,4-di-tertiary-butyl-phenyl) cyclohexyl phosphite and 2,4-di-(tertiary butyl)phenyl dicyclohexyl phosphite, which are liquids.

French Pat. No. 1,496,563 described phosphites derived from 2,6-di-tertiary-butyl-hydroquinone and 2,5-di-tertiary-butyl-hydroquinone, and it is suggested that they can be used with thiodipropionic acid esters of olefin polymers.

British Pat. No. 1,143,375 has a similar disclosure; tris-(2,5-di-tertiary-butyl-4-hydroxy-phenyl)phosphite is disclosed.

British Pat. No. 1,058,977 discloses 2,4,6-tri-substituted aryl phosphites, the substituents including tertiary-butyl groups.

French Pat. No. 1,497,390 discloses tris-(3,5-di-alkyl-4-hydroxy-phenyl)phosphites, as well as tris-(3-isopropyl-5-tertiary-butyl-phenyl)phosphite.

Kuriyama et al U.S. Pat. No. 3,558,554 patented Jan. 26, 1971, provides olefin polymer compositions containing as a stabilizer an organophosphite having the general formula:

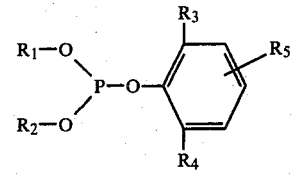

wherein $R_1$ and $R_2$ each represents a member selected from the group consisting of substituted and unsubstituted alkyl, cycloalkyl, aryl, alkaryl, aralkyl, and aliphatic thio ether groups and $R_3$, $R_4$ and $R_5$ each represents a member selected from the group consisting of hydrogen and alkyl, cycloalkyl, aryl, alkaryl, and aralkyl groups, at least one of said $R_3$ and $R_4$ being a tertiary butyl group.

Suitable organo phosphites include, for example, di-n-butyl(2-t-butyl-cresyl)phosphite, di-n-hexyl(2-t-butyl-m-cresyl)phosphite, di-n-hexyl(2-t-butyl-p-cresyl)phosphite, di-n-octyl(2-t-butyl-p-cresyl)phosphite, di-n-butyl-3,4-di-t-butyl-phenyl)phosphite, di-n-butyl-(2,6-di-t-butyl-p-cresyl)phosphite, di-phenyl(2-t-butyl-p-cresyl)phosphite, tri-(2-t-butyl-p-cresyl)phosphite, di-(ethylthioethyl)-(2-t-butyl-p-cresyl)phosphite, di(octylthioethyl) (2-t-butyl-p-cresyl)phosphite, and tri(2,4-di-t-butyl-phenyl)phosphite.

Many organic phosphites have been proposed as stabilizers for polyvinyl chloride resins, and are employed either alone or in conjunction with other stabilizing compounds, such as polyvalent metal salts of fatty acids and alkyl phenols. Such phosphite stabilizers normally contain alkyl or aryl radicals in sufficient number to satisfy the three valences of the phosphite, and typical phosphites are described in the patent literature, for example, W. Leistner et al., U.S. Pat. Nos. 2,564,646 of Aug. 14, 1951, 2,716,092 of Aug. 23, 1955, and 2,997,454 of Aug. 2, 1961.

Organic phosphites have also been added as stabilizers in amounts of 0.01 to 1%, preferably 0.05% to 0.2% by weight, to high molecular weight polycarbonate plastics, for example the polycarbonate of 2,2′-bis(4-hydroxyphenyl)propane of molecular weight 10,000 and up to over 50,000 as disclosed by G. Fritz in U.S. Pat. No. 3,305,520 of Feb. 21, 1967.

A. Hecker in U.S. Pat. No. 2,860,115 of Nov. 11, 1958 discloses compositions of organic phosphites with metal salts of carboxylic acids used in olefin polymers.

Phosphites are also employed in conjunction with other stabilizers such as a polyhydric phenol in the stabilization of polypropylene and other synthetic resins against degradation upon heating or ageing under atmospheric conditions. The polyhydric phenol is thought to function as an antioxidant in such combinations. Disclosures by R. Werkheiser, U.S. Pat. Nos. 2,726,226 of Dec. 6, 1975; I. Salyer et al, 2,985,617 of May 23, 1961; L. Friedman, 3,039,993 of June 19, 1962; W. Nudenberg, 3,080,338 of Mar. 5, 1963; C. Fuchsman, 3,082,187 of Mar. 19, 1963; H. Orloff et al, 3,115,465 of Dec. 24, 1963; A. Nicholson, 3,167,526 of Jan. 26, 1965; A. Hecker et al, 3,149,093 of Sept. 15, 1964, 3,244,650 of Apr. 5, 1966 and 3,225,136 and 3,255,151 of June, 7, 1966; C. Bawn, 3,352,820 of Nov. 14, 1967; D. Miller, 3,535,277 of Oct. 20, 1970; J. Casey, 3,586,657 of June 22, 1971; C. Abramoff 3,856,728 of Dec. 24, 1974; M. Minagawa, 3,869,423 of Mar. 4, 1975 and 3,907,517 of Sept. 23, 1975; and British Pat. Nos. 846,684, 851,670, and 866,883 are representative of stabilizer combinations including organic phosphites, polyhydric phenols, and other active ingredients.

The importance of organic phosphites as stabilizers for synthetic resins has led to the development of a large variety of special phosphites intended to provide improved stabilizing effectiveness and compatability and ease of compounding with the resin and with other stabilizers commonly used. However, the phosphites which have been proposed have not been entirely successful, partly because of their complicated structure, which makes them costly to prepare, and partly because of their difficulty of preparation.

Among these special phosphites, L. Friedman, U.S. Pat. No. 3,047,608 of July 31, 1962 discloses a class of biphosphites having the formula:

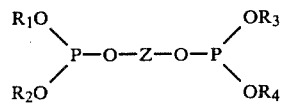

and

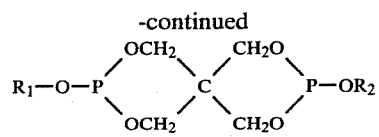

in which $R_1$, $R_2$, $R_3$ and $R_4$ are alkyl or aryl and Z is $-CH_2CH_2SCH_2CH_2O-$, $-C_2CH_2SO_2C_2CH_2-(-CH_2CH_2O-)_x$ or $(CHCH_3CH_2)_x$ where x is at least two, and in U.S. Pat. No. 3,053,878 of Sept. 11, 1962 a class of linear phosphite polymers having the formula:

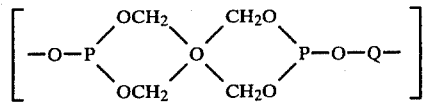

in which Q is the alkylene or arylene portion of a dihydric alcohol or dihydric phenol.

R. Morris et al in U.S. Pat. No. 3,112,286 of Nov. 26, 1963 discloses phosphites having the formula:

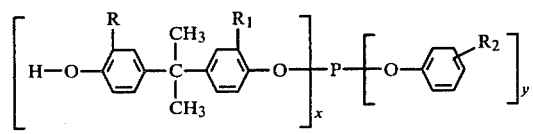

in which
R represents a bulky hydrocarbon group such as t-butyl, t-amyl, t-hexyl, cyclohexyl, t-pentyl, t-octyl, phenyl and the like;
$R_1$ represents hydrogen and R;
$R_3$ represents an alkyl group from six to twenty carbon atoms which is preferably in the meta or para position;
x represents a number of from 1 to 3 inclusive;
y represents a number of from 0 to 2 inclusive and the sum of the numerical value of x+y is always exactly 3.

D. Brown, U.S. Pat. No. 3,297,631 of Jan. 10, 1967 discloses condensation products of phosphorus compounds with bisphenols and trisphenols which may be represented by the structures:

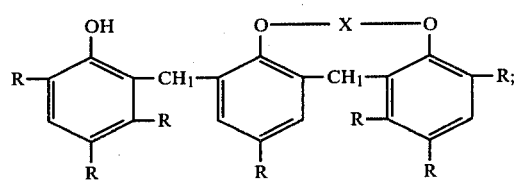

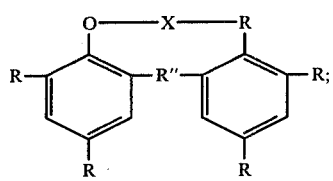

-continued

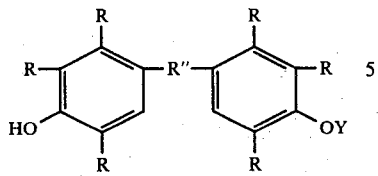

where: X is selected from the following: >P—OR'; >P—R';

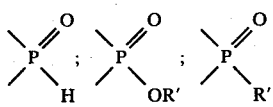

and Y is selected from the following: —P(OR')$_2$;

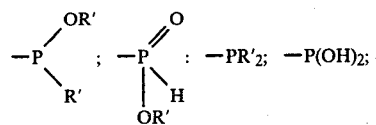

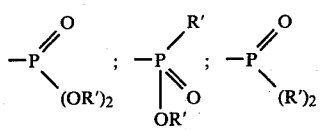

R is hydrogen, alkyl of one to sixteen carbon atoms or aryl or a combination of these; R' is alkyl of one to sixteen carbon atoms or aryl, and R" is alkylidene of one to sixteen carbon atoms or an aryl-substituted alkylidene.

C. Baranauckas, U.S. Pat. No. 3,305,608 of Feb. 21, 1967, discloses phenolic phosphites useful as polymer stabilizers prepared by reacting a triorganophosphite, a polyol, and an aromatic material having two to six phenolic hydroxyl groups at 60° to 180° C. in specified proportions.

C. Brindell, U.S. Pat. No. 3,412,064 of Nov. 19, 1968 discloses phenolic phosphites represented by the general formula:

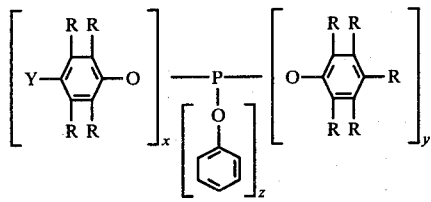

where x is from 1 to 3, y and z each from 0 to 2, x+y+z=3, R is hydrogen or alkyl and Y is hydroxyl or a group of the formula:

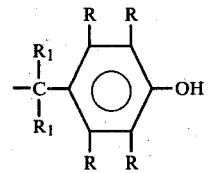

where R is hydrogen or alkyl.

M. Larrison, U.S. Pat. No. 3,419,524 of Dec. 31, 1968, discloses phosphites useful as polymer stabilizers having the formula:

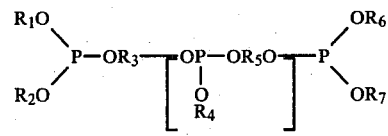

where $R_1$, $R_2$, $R_4$, $R_6$ and $R_7$ are aryl or haloaryl, and $R_3$ and $R_5$ are a polyalkylidene glycol or an alkylidene bisphenol or a hydrogenated alkylidene bisphenol or a ring-halogenated alkylidene bisphenol from which the two terminal hydrogens have been removed.

O. Kauder et al, U.S. Pat. Nos. 3,476,699 of Nov. 4, 1969 and 3,655,832 of Apr. 11, 1972 discloses organic phosphites containing a free phenolic hydroxyl group and defined by the formula:

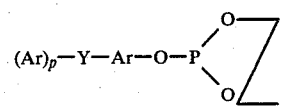

wherein Z is selected from the group consisting of hydrogen and aliphatic, cycloaliphatic, aromatic, heterocyclic and (Ar)$_p$-Y-Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic; thioaliphatic, oxycycloaliphatic, thiocycloaliphatic; heterocyclic, oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Friedman, U.S. Pat. No. 3,516,963 of June 23, 1970 discloses phosphites having the formula:

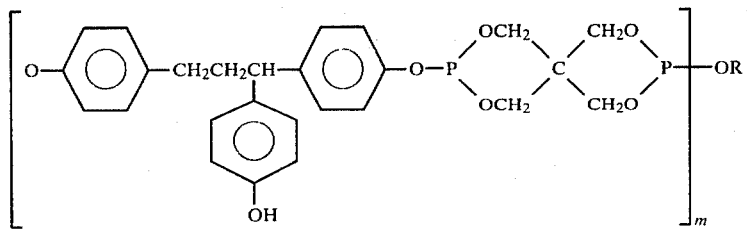

where R is alkyl, alkenyl, aryl, aralkyl, haloaryl, haloalkyl or

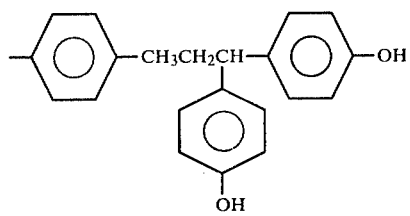

and n is an integer of at least 1. n can be 2, 3, 4, 5, 6, 7, 8, 10, 50, 100 or even more.

D. Bown et al in U.S. Pat. Nos. 3,510,507 of May 5, 1970 and 3,691,132 of Sept. 12, 1972 discloses polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula:

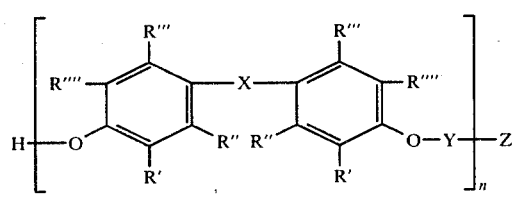

where X is selected from the group consisting of

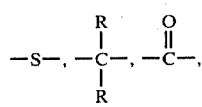

—C—C, and C—A—C— where A is a $C_1$ to $C_{16}$ alkylene or an arylene; R', R'', R''', and R'''' are selected from the group consisting of hydrogen, $C_1$ to $C_{18}$ alkyls, and an aryl group; Y is selected from the group of

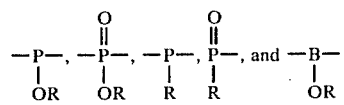

where R is hydrogen, a $C_1$ to $C_{18}$ alkyl or aryl;

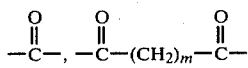

where m is 0 to 10, preferably 4 to 8,

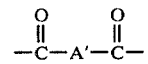

where A' is $(CH_2)_n$—S—$(CH_2)_n$ or —$(CH_2)_n$—S—$(CH_2)_m$—S—$(CH_2)_n$ where n is 0 to 10, preferably 2 and m is 0 to 10, preferably 5;

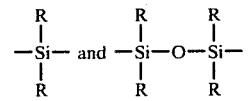

where R is an alkyl, preferably methyl, and Z is

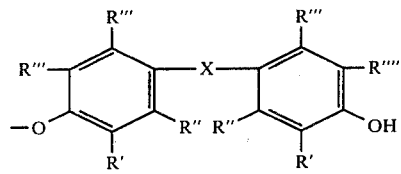

where R', R'', R''', R'''', and X correspond respectively to the R', R'', R''', R'''', and X previously selected when n has a value from 1 to 15, or may be derived from the compound used to introduce Y into the product when n has a value from 2 to 15, for example, —R or —OR where R is hydrogen, an alkyl, or aryl. When Y in the formula of Bown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto) paraxylylene, and 10, 24-dithiotetracontane.

J. Floyd et al in German published application No. 2505071 of Aug. 14, 1975 abstracted in *Chemical Abstracts* 1976, Volume 84, abstract No. 5945f, discloses low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris (nonyl-phenyl) phosphite, and distearyl pentaerythritol diphosphite.

In accordance with the present invention, there is provided a new class of hindered bisphenol phenyl phosphites having the general structure:

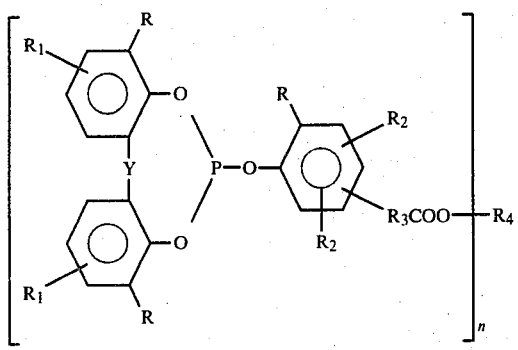

wherein:

- R is selected from the group consisting of alkyl having from one up to about eighteen carbon atoms; cycloalkyl having from three up to about twelve carbon atoms; alkaryl and aryl having from six to about eighteen carbon atoms; preferably, a bulky group such as iso, secondary or tertiary alkyl having from three to about ten carbon atoms; or cycloalkyl having six to twelve carbon atoms;
- $R_1$ and $R_2$ are each selected from the group consisting of hydrogen; alkyl having from one to about eighteen carbon atoms; cycloalkyl having from three up to about twelve carbon atoms; alkaryl and aryl having from six to about eighteen carbon atoms; and are preferably in a position ortho to a phenolic hydroxyl or phenoxy group, if available;
- $R_3$ is alkylene having from one to about six carbon atoms;
- $R_4$ is selected from the group consisting of alkylene, cycloalkylene, and aralkylene, the residue of a monohydric or polyhydric alcohol, having from one to about eighteen carbon atoms, and from none to three hydroxyl groups (originally one to four hydroxyl groups;
- Y is selected from the group consisting of a direct carbon to carbon bond; thio sulfur —S—; oxy oxygen —O—; alkylidene having from one to about six carbon atoms; and cycloalkylidene having from four to about eight carbon atoms; and
- n is 1, 2, 3, or 4, according to the valence of $R_4$.

Synthetic resin compositions are also provided having an enhanced resistance to deterioration by heat and/or light due to the presence therein of an organic phosphite of this class.

These phosphites are capable of enhancing the resistance to deterioration due to heat and/or light of synthetic resins as a class, when combined therewith in small amounts within the range from about 0.01 to about 10% by weight of the synthetic resin.

Exemplary R, $R_1$ and $R_2$ alkyl groups having from one to about eighteen carbon atoms include methyl, ethyl, propyl, isopropyl, butyl, secondary butyl, tertiary butyl, isobutyl, amyl, isoamyl, secondary amyl, tertiary amyl, hexyl, isohexyl, heptyl, octyl, 2-ethyl hexyl, isooctyl, nonyl, isononyl, decyl, isodecyl, lauryl, myristyl, palmityl, and stearyl.

R, $R_1$ and $R_2$ may also be cycloalkyl having about three to about twelve carbon atoms, including, for example, cyclopropyl, cyclobutyl, cyclopentyl, cyclohexyl, cycloheptyl, cyclooctyl, cyclododecyl and alkyl-substituted cycloalkyl such as 4-methyl cyclohexyl, 4-methyl cyclopentyl, and p-dimethyl cyclohexyl.

R, $R_1$ and $R_2$ alkaryl and aryl groups include phenyl, diphenyl benzyl, α-methyl benzyl, αα-dimethyl benzyl, α-methyl, naphthyl, tolyl, xylyl, ethylphenyl, butylphenyl, tertiary butylphenyl, octylphenyl, 2,6-di-t-butyl-4-methylphenyl, 2,6-di-t-butyl-4-methoxycarbonyl ethylphenyl, isooctylphenyl, t-octylphenyl, nonylphenyl, 2,4-di-t-butylphenyl, cyclohexylphenyl, cyclooctylphenyl, 4-methoxyphenyl, 4-ethoxyphenyl, 3-lauroxyphenyl, 2-methoxy-4-methylphenyl, 2-t-butyl-4-methoxyphenyl, 4-benzyloxyphenyl, and 3, 4-methylenedioxyphenyl.

Preferably, R is a bulky group, an iso, secondary or tertiary alkyl group having from three to about ten carbon atoms, such as isopropyl, secondary butyl, tertiary butyl, iso amyl, tertiary amyl, or tertiary octyl, or a cycloalkyl group of six to twelve carbon atoms, such as cyclohexyl, methylcyclohexyl, cycloheptyl or cyclooctyl.

Exemplary Y alkylidene and cycloalkylidene groups include methylene, isopropylidene, butylidene, cyclohexylidene and isopropylbenzylidene.

$R_4$ is the residue of a polyhydric alcohol having from one to about four hydroxyl groups capable of being esterified with trivalent phosphorus of a phosphite, of which at least one such group is taken up by phosphorus and the remaining group or groups may be taken up with phosphorus or may be free, such as, for example, methanol, ethanol, isopropanol, butanol, isobutanol, octanol, isooctanol, nonanol, isodecanol, tridecanol, lauryl alcohol, stearyl alcohol, cetyl alcohol, myristyl alcohol, oleyl alcohol, cyclohexanol, benzyl alcohol, ethylene glycol, glycerol, erythritol, pentaerythritol, trimethylol ethane, trimethylol propane, trimethylol butane, 1,2-propanediol, 1,3-propanediol, 1,2-butanediol, 1,4-butanediol, neopentylglycol, thiodiethyleneglycol, 1,6-hexanediol, 1,10-decanediol, 1,4-cyclohexanediol, 1,4-cyclohexanedimethanol, 1,4-phenylenedimethanol, hydrogenated Bisphenol A, ditrimethylolethane, ditrimethylolpropane, and tris(2-hydroxyethyl) isocyanurate.

Also included are the polyoxyalkylene polyols containing one or more oxyalkylene groups with terminal hydroxyls free or etherified with alkyl, cycloalkyl or phenyl groups having from one to about ten carbon atoms. Exemplifying this class are methyl Cellosolve, ethyl Cellosolve, isopropyl Cellosolve, butyl Cellosolve, hexyl Cellosolve, cyclohexyl Cellosolve, and phenyl Cellosolve; methyl Carbitol, ethyl Carbitol, isopropyl Carbitol, butyl Carbitol and isobutyl Carbitol; dipropylene glycol, diethylene glycol, triethylene glycol, triethylene glycol monomethyl ether, triethylene glycol monoethyl ether, triethylene glycol monobutyl ether, glyceryl 1,2-dimethyl ether, glyceryl 1,3- dimethyl ether, glyceryl 1,3-diethyl ether and glyceryl 1-ethyl-2-propyl ether; nonyl phenoxy; polyethoxy ethyl, and lauroxy polyethoxyethyl.

Exemplary hindered bisphenols of the structure:

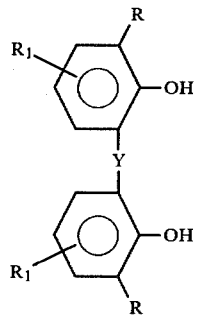

include 2,2′-methylenebis(4-methyl-6-t-butylphenol), 2,2′-methylenebis(4-ethyl-6-t-butylphenol), 2,2′-methylenebis(4-ethyl-6-t-butylphenol), 2,2′-methylenebis [4-methyl-6-(α-methylcyclohexyl) phenol], 2,2′-n-butylidenebis(4,6-dimethylphenol), bis-1,1-(2′-hydroxy-3′,5′-dimethylphenyl)-3,5,5-tri-methylhexane, 2,2′-cyclohexylidenebis(4-ethyl-6t-butylphenol), 2,2′-isopropylbenzylidene-bis(4-ethyl-6-t-butylphenol), 2,2′-thiobis(4-t-butyl-6-methylphenol), 2,2′-thiobis(4-methyl-6-t-butylphenol), 2,2′-thiobis (4,6-di-t-butylphenol), 2,2′-methylenebis(4-α-methylbenzyl-6-cyclohexylphenol), 2,2′-methylenebis(4-cyclohexyl-6-α-methylbenzylphenol), 2,2′-dihydroxybiphenyl, 2,2′-dihydroxy-3,3′,5,5′-tetra-t-butylbiphenyl, 2,2′-dihydroxy-3,3′,5,5′-tetra-t-amylbiphenyl, 2,2′-dihydroxy-3,3′,5,5′-tetra-t-octylbiphenyl, bis (2-hydroxy-3-t-butylphenyl) ether and bis (2-hydroxy-3-propylphenyl) ether.

The following compounds are exemplary:

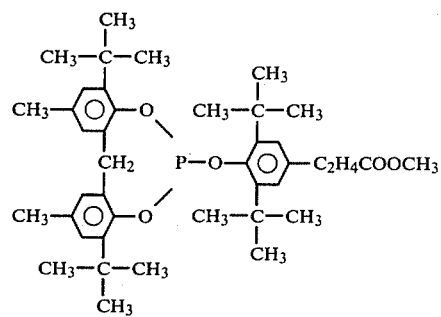

1.

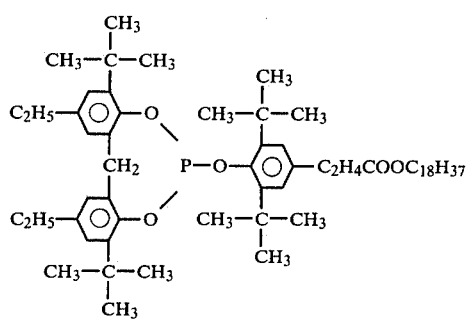

2.

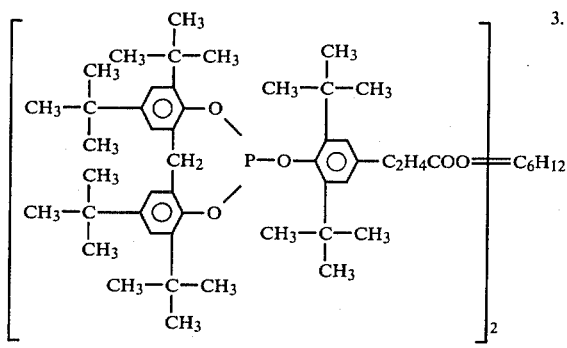

3.

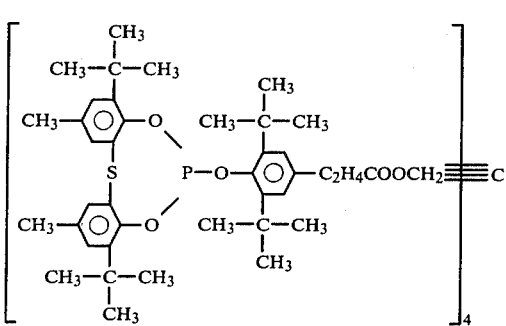

4.

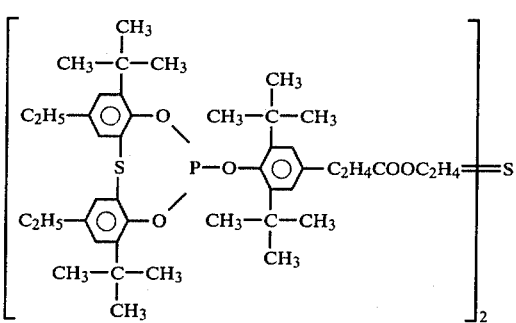

5.

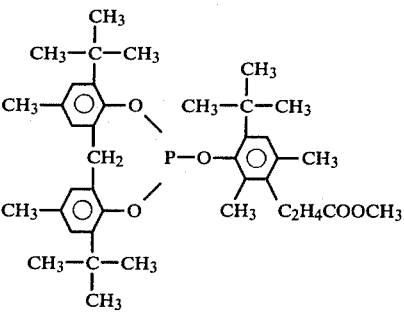

6.

7.
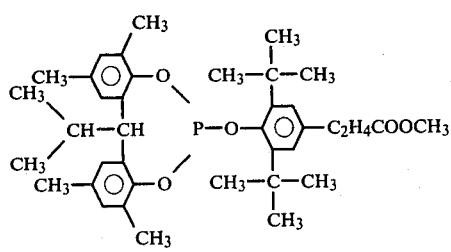
8.
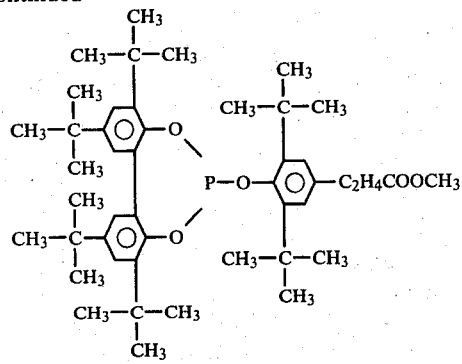
9.
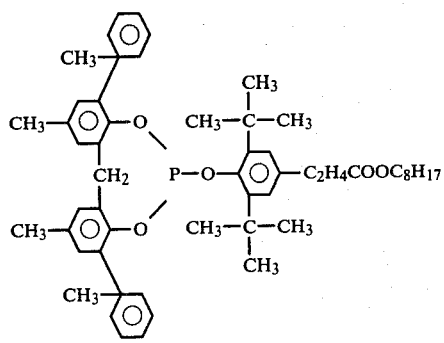
10.
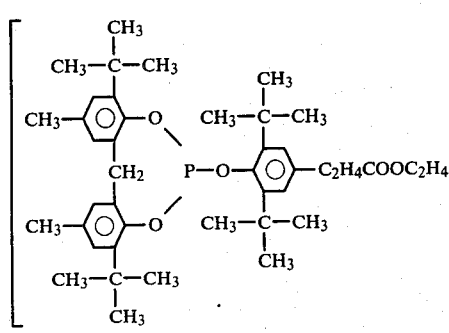
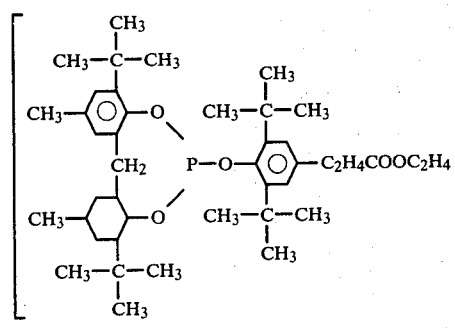
11.
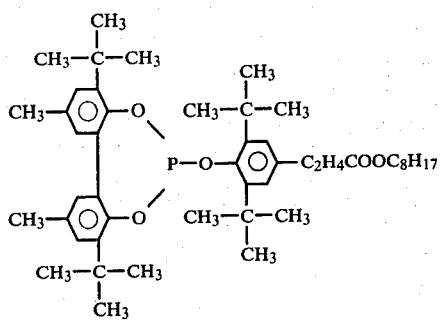
12.

13.

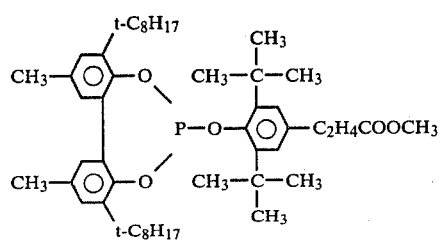

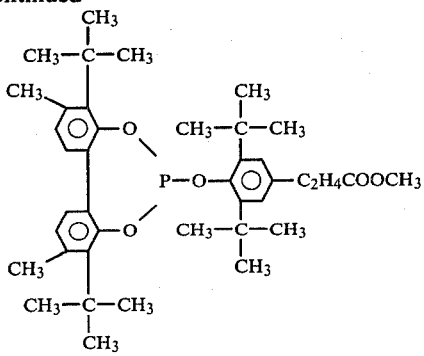

14.

15.

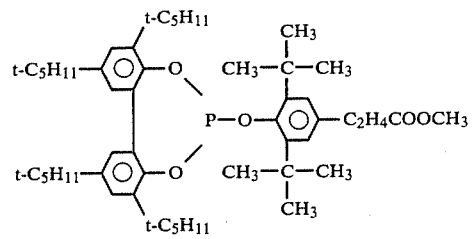

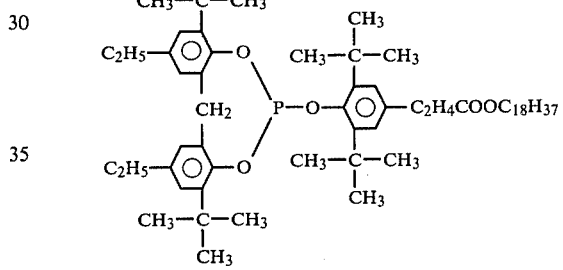

These phosphites are readily prepared by conventional procedures. Thus, for example, the corresponding hindered bis phenol

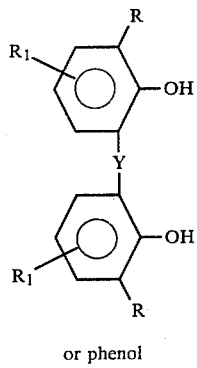

or phenol

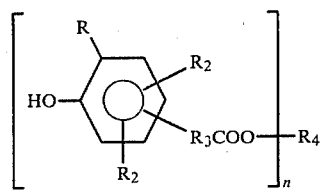

can be reacted with phosphorus trichloride, trimethyl phosphite or triphenyl phosphite in the presence of a base, such as an amine catalyst, to form the phosphite. Conventional transesterification procedures can also be used.

The following Example serves to illustrate the procedure:

EXAMPLE I

Preparation of

To a solution of 200 ml toluene, 36.8 g 2,2'-methylenebis (4-ethyl-6-t-butylphenol) and 22.2 g triethylamine, 13.8 g of phosphorus trichloride was added dropwise over one hour. Then the whole was stirred for ten hours at room temperature. The hydrochloric acid salt of triethylamine was filtered out, and solvent was stripped from the reaction mixture.

This intermediate was dissolved in 50 ml of toluene, and this solution was added dropwise to a solution of 53 g of octadecyl 3-(3,5-di-t-butyl-4-hydroxyphenyl)propionate, 12.1 g of triethylamine and 200 ml of toluene over one hour. The whole was refluxed for ten hours. The hydrochloric acid salt of triethylamine was filtered out, and solvent was distilled off.

A white powder having the m.p. 56° to 70° C. was obtained.

The phosphites of the invention are especially effective in enhancing the resistance to deterioration by heat and light of polyvinyl chloride resins. The term "polyvinyl chloride" as used herein is inclusive of any polymer formed at least in part of the recurring group:

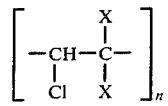

and having chlorine content in excess of 40%. In this group, the X groups can each be either hydrogen or chlorine, and n is the number of such units in the polymer chain. In polyvinyl chloride homopolymers, each of the X groups is hydrogen. Thus, the term includes not only polyvinyl chloride homopolymers but also after-chlorinated polyvinyl chlorides as a class, for example, those disclosed in British Pat. No. 893,288 and also copolymers of vinyl chloride in a major proportion and other copolymerizable monomers in a minor proportion, such as copolymers of vinyl chloride and vinyl acetate, copolymers of vinyl chloride with maleic or fumaric acids or esters, and copolymers of vinyl chloride with styrene. The phosphites are effective also with mixtures of polyvinyl chloride in a major proportion with a minor proportion of other synthetic resins such as chlorinated polyethylene or a copolymer of acrylonitrile, butadiene and styrene.

The phosphites are applicable to the stabilization of rigid polyvinyl chloride resin compositions, that is, resin compositions which are formulated to withstand high processing temperatures, of the order of 375° F. and higher, as well as plasticized polyvinyl chloride resin compositions of conventional formulation, even though resistance to heat distortion is not a requisite. Conventional plasticizers well known to those skilled in the art can be employed such as, for example, dioctyl phthalate, octyl diphenyl phosphate and epoxidized soybean oil.

Particularly useful plasticizers are the epoxy higher esters having from 20 to 150 carbon atoms. Such esters will initially have had unsaturation in the alcohol or acid portion of the molecule, which is taken up by the formation of the epoxy group.

Typical unsaturated acids are acrylic, oleic, linoleic, linolenic, erucic, ricinoleic, and brassidic acids, and these may be esterified with organic monohydric or polyhydric alcohols, the total number of carbon atoms of the acid and the alcohol being within the range state. Typical monohydric alcohols include butyl alcohol, 2-ethyl hexyl alcohol, lauryl alcohol, isooctyl, alcohol, stearyl alcohol, and oleyl alcohol. The octyl alcohols are preferred. Typical polyhydric alcohols include pentaerythritol, glycerol, ethylene glycol, 1,2-propylene glycol, 1,4-butylene glycol, neopentyl glycol, ricinoleyl alcohol, erythritol, mannitol and sorbitol. Glycerol is preferred. These alcohols may be fully or partially esterified with the epoxidized acid. Also useful are the epoxidized mixtures of higher fatty acid esters found in naturally-occurring oils such as epoxidized soybean oil, epoxidized olive oil, epoxidized coconut oil, epoxidized cottonseed oil, epoxidized tall oil fatty acid esters and epoxidized tallow. Of these, epoxidized soybean oil is preferred.

The alcohol can contain the epoxy group and have a long or short chain, and the acid can have a short or long chain, such as epoxystearyl acetate, epoxystearyl stearate, glycidyl stearate, and polymerized glycidyl methacrylate.

The polyvinyl chloride resin can be in any physical form, including, for example, powders, films, sheets, molded articles, foams, filaments, and yarns.

A sufficient amount of the phosphite is used to enhance the resistance of the polyvinyl chloride to deterioration in physical properties, including, for example, discoloration and embrittlement, under the heat and/or light conditions to which the polymer will be subjected. Very small amounts are usually adequate. Amounts within the range from about 0.01 to about 5% by weight of the polyvinyl chloride resin are satisfactory. Preferably, an amount within the range from about 0.05 to about 2% is employed, for optimum stabilizing effectiveness.

The phosphites of the invention can be employed as the sole stabilizer. They can also be used in combination with other conventional heat and light stabilizers for polyvinyl chloride resins, such as, for example, polyvalent metal salts, alkaline earth metal phenolates, and phenolic antioxidants, as well as epoxy compounds.

A particularly useful stabilizer system contains the following amounts of ingredients:
 (a) phosphite in an amount within the range from about 25 to about 45 parts by weight;
 (b) polyvalent metal salt of an aliphatic carboxylic acid or of an alkyl phenol in an amount within the range from about 25 to about 45 parts by weight;
 plus any one or more of the following optional ingredients:
 (c) phenolic antioxidant in an amount within the range from about 0.01 to about 1 part by weight;
 (d) free aliphatic carboxylic acid in an amount within the range from about 0.5 to about 5 parts by weight, but in no case more than 15% by weight of the cadmium carboxylate; and
 (e) acid phosphite in an amount within the range from about 0.5 to about 5 parts by weight.

In addition, any of the conventional polyvinyl chloride resin additives, such as lubricants, emulsifiers, antistatic agents, flame-proofing agents, pigments and fillers, can be employed.

Preferably, the stabilizer system is added to the polyvinyl chloride resin in an amount to provide in the resin from about 0.1 to about 2% of polyvalent metal salt or phenolate; from about 0.2 to about 1% of the phosphite; and from about 0 to about 1% total of one or more of the additional ingredients, as noted above.

The stabilizer system is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polyvinyl chloride resin can be worked into the desired shape, such as by milling, calendering, extrusion or injection molding, or fiber-forming. In such operations, it will be found to have a considerably improved resistance to discoloration and embrittlement on exposure to heat and light.

The phosphites of the invention are especially effective heat stabilizers for olefin polymers such as polyethylene, polypropylene, polybutylene, polypentylene, polyisopentylene, and higher polyolefins.

Olefin polymers on exposure to elevated temperatures undergo degradation, resulting in embrittlement and discoloration.

The stabilizer systems can be employed with any olefin polymer, including low-density polyethylene, high density polyethylene, polyethylenes prepared by the Ziegler-Natta process, polypropylenes prepared by the Ziegler-Natta process, and by other polymerization methods from propylene, poly(butene-1), poly(pentene-1),poly(3-methylbutene-1)poly(4-methyl-pentene-1), polystyrene, and mixtures of polyethylene and polypropylene with other compatible polymers, such as mixtures of polyethylene and polypropylene, and copolymers of such olefins, such as copolymers of ethylene, propylene, and butene, with each other and with other copolymerizable monomers. The term "olefin polymer" encompasses both homopolymers and copolymers.

Polypropylene solid polymer can be defined in a manner to differentiate it from other polyolefins as having a density within the range from 0.86 to 0.91, and a melting point above 150° C. The phosphites of the invention are applicable to all such polypropylenes, as distinguished from polypropylenes in the liquid form or in semiliquid of gel-like forms, such as are used as greases and waxes.

The phosphites of the invention are applicable to polypropylenes prepared by any of the various procedures, for the molecular weight and tacticity are not factors affecting this stabilizer system. Isotactic polypropylene, available commercially under the trade name PRO-FAX, and having a softening or hot-working temperature of about 350° F., is an example of a sterically regular polypropylene polymer.

Mixtures of polypropylene with other compatible polymers and copolymers of propylene with copolymerizable monomers not reactive with the phosphite or stabilizer combination can also be stabilized, for example, mixtures of polyethylene and polypropylene, and copolymers of propylene and ethylene.

The phosphites are also effective to enhance the resistance to heat degradation of polystyrene; polydienes, such as polybutadiene and polyisoprene; and copolymers of olefins and dienes with other ethylenically and acetylenically unsaturated monomers, such as ethylene-vinyl acetate copolymers, styrene-butadiene copolymers, acrylonitrile-styrene-butadiene copolymers, synthetic rubbers of all types, such as polychloroprene; polyvinylidene chloride; and copolymers of vinyl chloride and vinylidene chloride; vinylidene chloride and vinyl acetate; and other ethylenically unsaturated monomers; polyacetals such as polyoxymethylene and polyoxyethylene; polycarbonates; polyphenylene oxides; polyesters such as polyethylene glycol-terephthalic acid ester polymers; polyamides such as poly-epsilon-caprolactam; polyhexamethylene adipamide and polydecamethylene adipamide; polyurethanes; and epoxy resins.

The synthetic polymer can be in any physical form, including (for example) filaments, yarns, films, sheets, molded articles, latex and foam.

A sufficient amount of the phosphite and any stabilizer combination including the phosphite is used to improve the resistance of the synthetic polymer to deterioration in physical properties, including, for example, discoloration, reduction in melt viscosity and embrittlement, under the conditions to which the polymer will be subjected. Very small amounts are usually adequate. Amounts within the range of from about 0.001 to about 5% total stabilizers by weight of the polymer are satisfactory. Preferably, from 0.01 to 3% is employed, for optimum stabilization.

The phosphites of the invention can be employed as the sole stabilizer or in combination with phenolic antioxidants and/or other conventional heat and light stabilizers for the particular olefin polymer.

Thus, for example, there can be employed fatty acid salts of polyvalent metals, phenolic antioxidants, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salt of divalent manganese can be used.

With synthetic rubbers and acrylonitrile-butadiene-styrene terpolymers, phenolic antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples illustrate preferred phosphite stabilizer systems and resin compositions of the invention:

EXAMPLES 1 TO 10

Polypropylene compositions were prepared using phosphites of the invention and having the following formulation:

| Ingredient | Parts by Weight |
|---|---|
| Polypropylene (Profax 6501) | 100 |
| Ca stearate | 0.2 |
| Pentaerythritol tetrakis (3,5-di-t-butyl-4-hydroxyphenyl) propionate | 0.1 |
| Dilauryl thiodipropionate | 0.2 |
| Phosphite as shown in Table I | 0.1 |

The composition was thoroughly blended for five minutes on a two roll mill at 180° C. The mixture was then compression molded at 250 kg/cm$^2$ and 180° C. for five minutes to form sheets 1 mm thick.

Pieces 2.5 cm$^2$ were cut off from the sheets and heated at 160° C. in a Geer oven to evaluate heat stability.

The time in hours required for the sheet to develop a noticeable discoloration and/or embrittlement was noted as the hours to failure.

The yellowness of the sheet after exposure to ultraviolet light for 72 hours was measured in a Hunter color difference meter.

The results obtained are shown in Table I.

TABLE I

| | Phosphite | Heat Stability (hours to failure) | Yellowness % Original | Yellowness % After 72 hours |
|---|---|---|---|---|
| Control | | | | |
| | None | 357 | 11.8 | 16.2 |
| 1 | Tris(2,4-di-t-butylphenyl) phosphite | 386 | 10.3 | 14.0 |
| 2 | [structure] | 457 | 12.0 | 17.6 |
| Example No. | | | | |
| 1 | [structure] | 850 | 8.5 | 11.0 |
| 2 | [structure] | 856 | 8.3 | 10.8 |
| 3 | [structure] | 840 | 8.4 | 10.7 |

TABLE I-continued
| Phosphite | Heat Stability (hours to failure) | Yellowness % Original | After 72 hours |
|---|---|---|---|
| 4 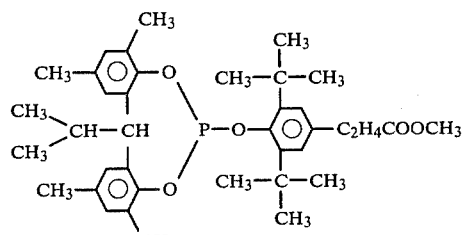 | 820 | 9.1 | 11.2 |
| 5 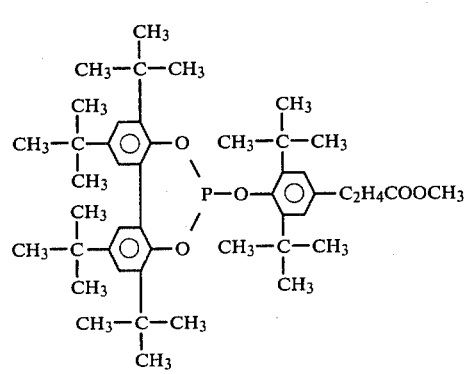 | 782 | 8.8 | 10.9 |
| 6 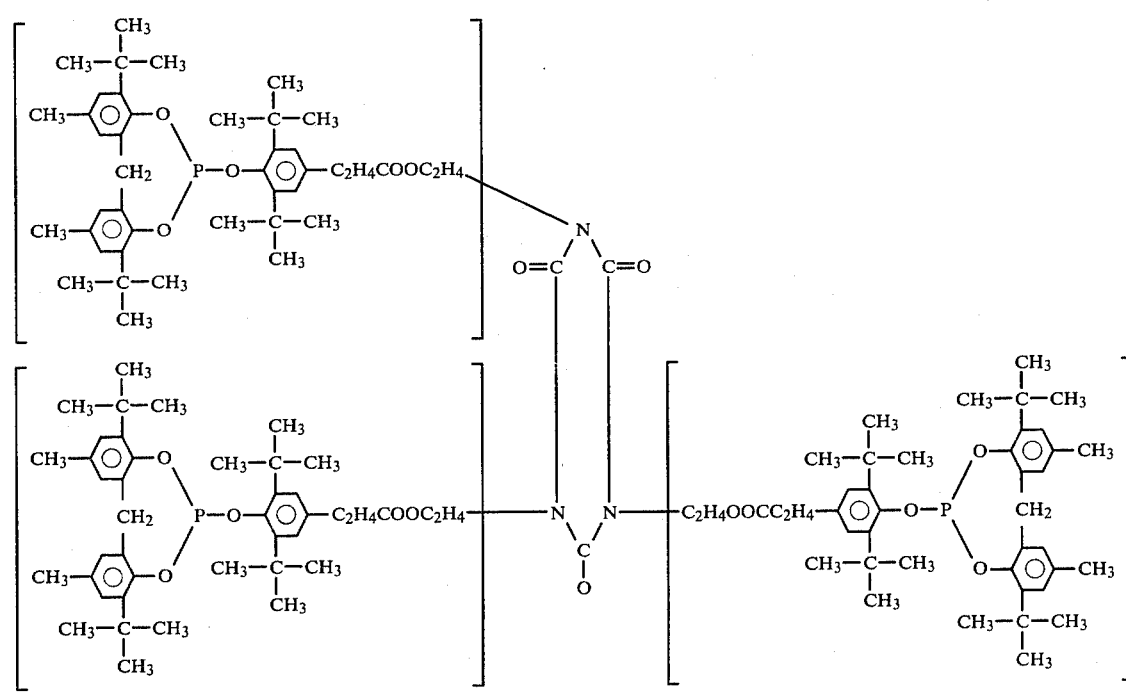 | 886 | 8.4 | 10.8 |

TABLE I-continued

| | Phosphite | Heat Stability (hours to failure) | Yellowness % Original | Yellowness % After 72 hours |
|---|---|---|---|---|
| 7 | (structure) | 893 | 8.3 | 10.0 |
| 8 | (structure) | 840 | 9.0 | 10.7 |
| 9 | (structure) | 870 | 8.9 | 10.4 |
| 10 | (structure) | 872 | 8.2 | 10.6 |

It is apparent from the above results that the phosphites of the invention are superior to the controls in enhancing resistance of the polypropylene polymer composition to deterioration when heated and when exposed to ultraviolet light.

EXAMPLES 11 TO 20

High density polyethylene compositions were prepared using phosphites of the invention, and having the following formulation:

| Ingredient | Parts by Weight |
|---|---|
| High-density polyethylene (Hizex 5100E) | 100 |
| Distearyl thiodipropionate | 0.3 |
| Stearyl 3(3-5-di-t-butyl-4-hydroxyphenyl) propionate | 0.1 |
| Phosphite as shown in Table II | 0.05 |

The stabilizers were blended with the polymer on a two-roll mill at 150° C. for five minutes, and sheets 1.2 mm thick were prepared by compression molding of the blend at 150° C. and 180 kg/cm² pressure for five minutes.

Pieces 10×20 mm were cut off from the sheets, and heated at 150° C. in a Geer oven on aluminum foil.

The time in hours when degradation set in, as determined by a significant discoloration and/or embrittlement, was noted as hours to failure.

The results are reported in Table II.

TABLE II

| Phosphite | Hours to Failure |
|---|---|
| Control | |
| None | 283 |
| Example No. | |
| 1 (structure) | 390 |
| 11 (structure) | 623 |
| 12 (structure) | 615 |
| 13 (structure) | 650 |

TABLE II-continued

| Phosphite | | Hours to Failure |
|---|---|---|
| 14 | [structure: bis phosphite with di-t-butyl/ethyl phenol groups bridged by S, with C₂H₄COOC₂H₄—S linker]₂ | 590 |
| 15 | [structure: phosphite with two 3-t-butyl-5-methylphenol groups bridged by CH₂, with O-aryl-C₂H₄COOCH₃ group] | 624 |
| 16 | [structure: phosphite with two 2,6-dimethylphenol groups bridged by CH(CH₃)₂-CH, with di-t-butyl-aryl-C₂H₄COOCH₃ group] | 604 |
| 17 | [structure: phosphite with two 3,5-di-t-butylphenol groups bridged, with di-t-butyl-aryl-C₂H₄COOCH₃ group] | 594 |
| 18 | [structure: phosphite with two 2-cyclohexyl-6-methylphenol groups bridged by CH₂, with di-t-butyl-aryl-C₂H₄COOC₈H₁₇ group] | 605 |

TABLE II-continued

| Phosphite | Hours to Failure |
|---|---|
| 19 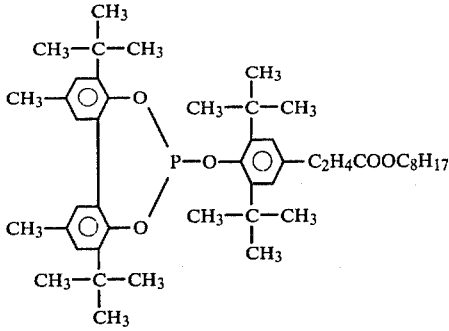 | 576 |
| 20 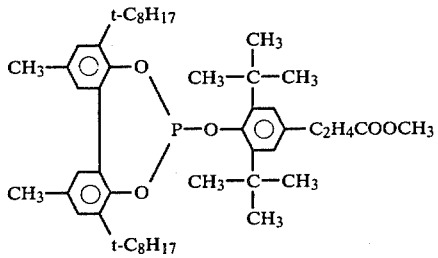 | 621 |

It is apparent from the above results that the phosphites of the invention are superior stabilizers in enhancing the resistance of the polyethylene polymer composition to deterioration when exposed to heat.

EXAMPLES 21 TO 26

Resin compositions having the following composition were prepared:

| Ingredient | Parts by Weight |
|---|---|
| Poly(2,6-dimethyl-1-4-phenyleneoxide) | 50 |
| Polystyrene | 47.5 |
| Polycarbonate | 2.5 |
| TiO$_2$ | 3 |
| Phosphite as shown in TABLE III | 0.5 |

The ingredients were mixed and then extruded at 60 rpm, 260° C., followed by injection molding at 290° C. to prepare the test pieces. The heat stability ws evaluated by heating the test pieces in a Geer oven at 125° C. for 100 hours. Elongation and Izod impact strength were measured before and after the heating, and the percent elongation and percent Izod impact strength retained were calculated.

The results are shown in Table III.

TABLE III

| | Phosphite | % Elongation Retained | % Impact Strength Retained |
|---|---|---|---|
| Control | | | |
| 1 | Tris(2-t-butyl-4-methylphenyl)phosphite | 42 | 40 |
| 2 | 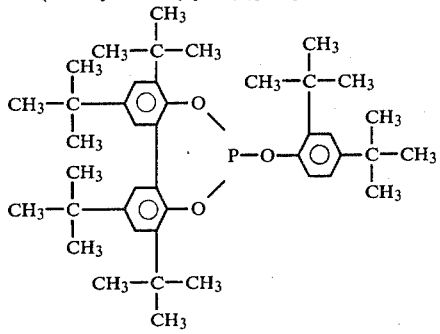 | 45 | 43 |

TABLE III-continued

| Example No. | Phosphite | % Elongation Retained | % Impact Strength Retained |
|---|---|---|---|
| 21 | (structure with bis-phenol methylene-bridged phosphite, aryl group with C₂H₄COOC₁₈H₃₇) | 67 | 65 |
| 22 | [bis-phenol methylene-bridged phosphite with aryl-C₂H₄COO–C₆H₁₂]₂ | 68 | 74 |
| 23 | [bis-phenol thio-bridged phosphite with aryl-C₂H₄COOCH₂–C≡C]₄ | 73 | 71 |
| 24 | [bis-phenol thio-bridged phosphite with aryl-C₂H₄COOC₂H₄–S]₂ | 69 | 74 |

TABLE III-continued

| | Phosphite | % Elongation Retained | % Impact Strength Retained |
|---|---|---|---|
| 25 | [structure: bis(2-methyl-4-cyclohexyl-6-methylphenyl)methylene phosphite with 2,6-di-t-butyl-4-(C₂H₄COOC₈H₁₇)phenyl ester] | 67 | 72 |
| 26 | [structure: bis(2,4-di-t-butyl-6-methylphenyl)methylene phosphite with 2,6-di-t-butyl-4-(C₂H₄COOC₈H₁₇)phenyl ester] | 70 | 68 |

The phosphites of the invention are clearly more effective heat stabilizers than the Controls.

EXAMPLES 27 TO 35

Acrylonitrile-butadiene-styrene terpolymer resin compositions were prepared using phosphites of the invention and having the following formulation:

| Ingredient | Parts by Weight |
|---|---|
| Acrylonitrile-butadiene-styrene terpolymer (Blendex 111) | 100 |
| Zinc stearate | 0.5 |
| Tris(3,5-di-t-butyl-4-hydroxyphenyl propionyl oxyethyl)isocyanurate | 0.1 |
| Phosphite as shown in TABLE IV | 0.3 |

The stabilizers were blended with the resin on a two-roll mill followed by compression molding at 160° C. of the resulting blend to prepare sheets 0.5 mm thick.

Heat stability was evaluated by heating the specimen sheets at 135° C. in a Geer oven for twenty hours. The whiteness of the specimens was evaluated using a Hunter color difference meter.

The results are shown in Table IV.

TABLE IV

| | Phosphite | Whiteness |
|---|---|---|
| Control | None | 16 |
| 1 | Tris(2-t-butylphenyl)phosphite | 21 |
| 2 | [structure: tris phosphite of bis(3-t-butyl-5-methyl-2-hydroxyphenyl)methane derivative] | 25 |

TABLE IV-continued
| Example No. | Phosphite | Whiteness |
|---|---|---|
| 27 | 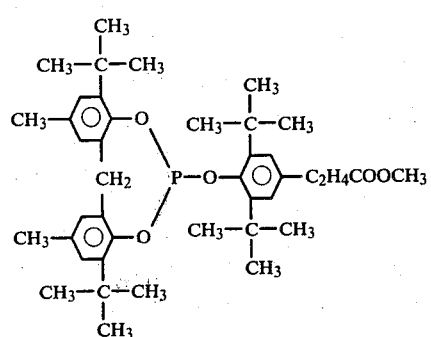 | 41 |
| 28 | 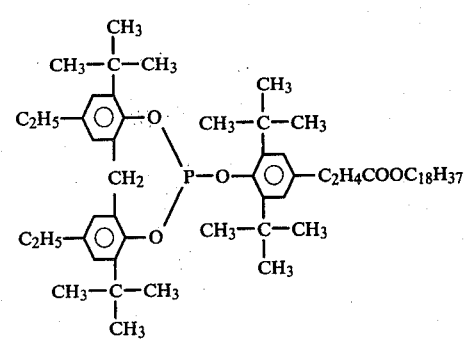 | 42 |
| 29 | 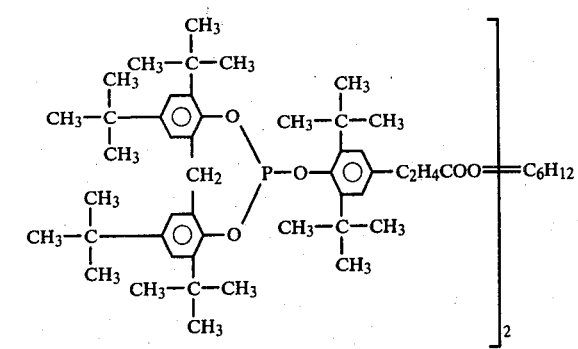 | 40 |
| 30 | 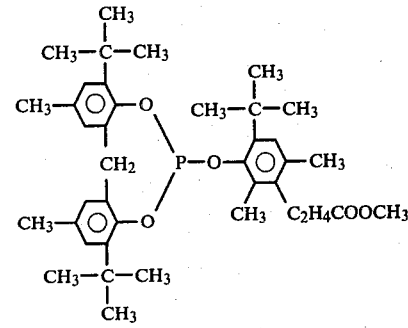 | 39 |
| 31 | 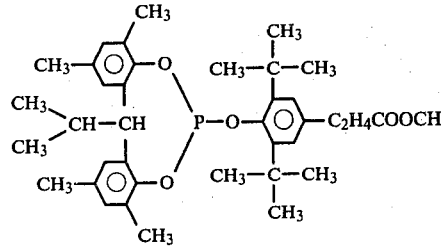 | 43 |
| 32 | | 43 |

TABLE IV-continued

| Phosphite | Whiteness |
|---|---|
| 33 (complex bis-phosphite structure with tert-butyl groups, methylene bridge, C₂H₄COOC₂H₄ linker to imide N-C(=O)-N-C(=O)) | 40 |
| 34 (bis-phosphite structure linked via C₂H₄COOC₂H₄—N—C(=O)—N—C₂H₄OOCC₂H₄) | 42 |
| 35 (phosphite with cyclohexyl-substituted phenol, CH₂ bridge, tert-butyl phenol with C₂H₄COOCH₃) | 44 |

(Structures as drawn: phosphites numbered 33, 34, 35 in left column; whiteness values 40, 42, 44 in right column — corresponding to compounds with biphenyl/dibenzo[d,f][1,3,2]dioxaphosphepine cores bearing t-butyl or t-C₅H₁₁ substituents and C₂H₄COOCH₃ pendant groups.)

It is apparent from the data that the phosphites of the invention are far superior to the Controls.

A group of polyvinyl chloride resin compositions was prepared having the following formulation:

| Ingredient | Parts by Weight |
|---|---|
| Polyvinyl chloride(Geon 103 EP) | 100 |
| Dioctyl phthalate | 42 |
| Epoxidized soybean oil | 3 |
| Zn stearate | 0.3 |
| Ba stearate | 0.5 |
| Stearic acid | 0.3 |
| 4,4'-n-butylidene-bis-(2-t-butyl-5-methyl phenol) | 0.05 |
| Phosphite shown in Table V | 0.2 |

This formulation was blended and sheeted off on a two-roll mill at 175° C. for five minutes and then compression molded at 180° C. to form clear sheets 1 mm thick.

The sheets were heated in air in a Geer oven at 190° C. to evaluate heat stability, and the time in minutes noted for the sheet to develop a noticeable discoloration and/or embrittlement.

Wet heat stability was also determined by heating at 175° C. in an atmosphere at 100% relative humidity, and again minutes to the development of a noticeable discoloration noted.

The results are shown in Table V.

TABLE V

| | Phosphite | Heat Stability at 190° C. (minutes) | Wet Heat Stability at 175° C. (minutes) |
|---|---|---|---|
| Control | | | |
| | None | 45 | 75 |
| 1 | Tris(2,4-di-t-butylphenyl)phosphite | 90 | 95 |
| 2 | Octyldiphenyl phosphite | 85 | 80 |
| 3 | 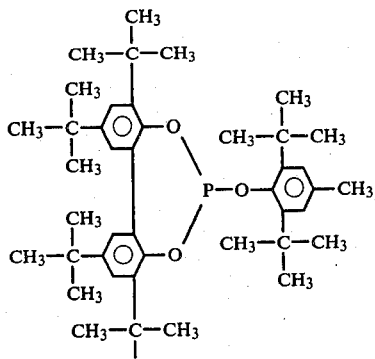 | 80 | 95 |
| Example No. | | | |
| 36 | 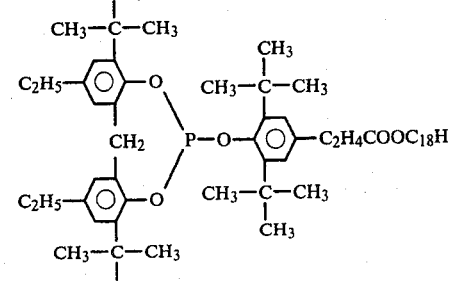 | 105 | 130 |
| 37 | 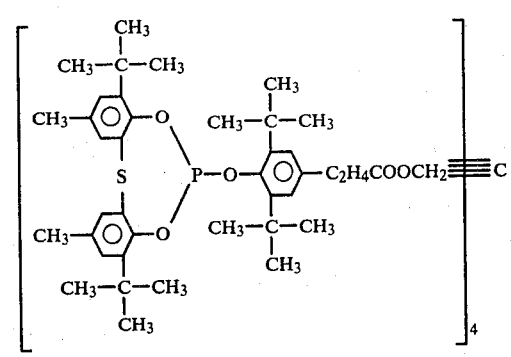 | 105 | 130 |

TABLE V-continued
| Phosphite | Heat Stability at 190° C. (minutes) | Wet Heat Stability at 175° C. (minutes) |
|---|---|---|
| 38 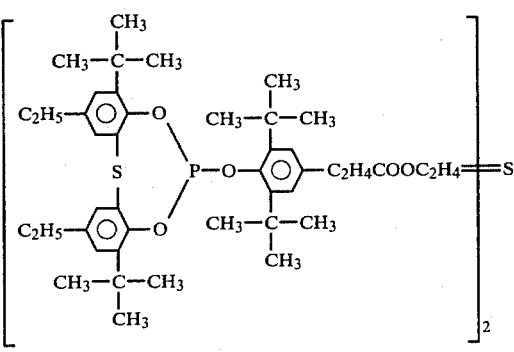 | 100 | 130 |
| 39 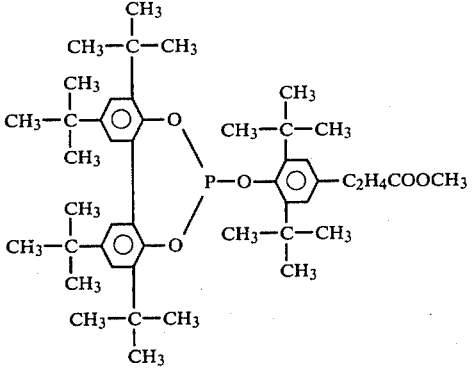 | 110 | 140 |
| 40 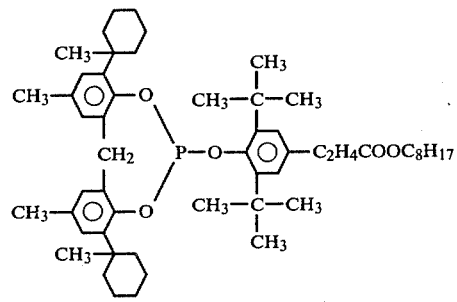 | 115 | 150 |

TABLE V
| Phosphite | Heat Stability at 190° C. (minutes) | Wet Heat Stability at 175° C. (minutes) |
|---|---|---|
| 41 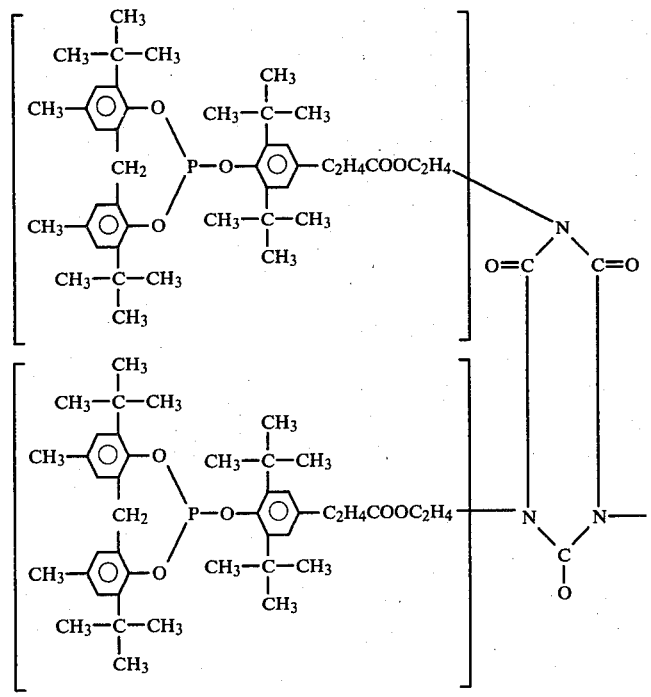 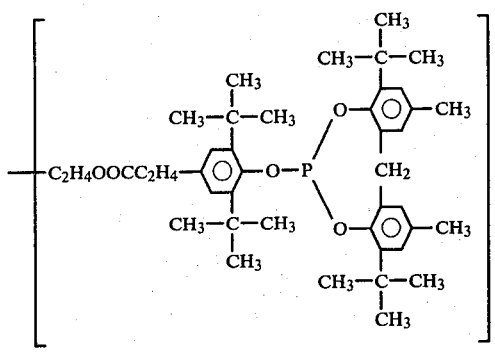 | 115 | 150 |
| 42 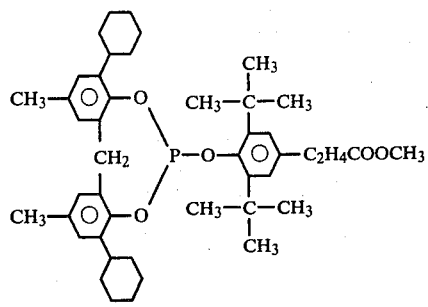 | 110 | 140 |

TABLE V-continued

| | Phosphite | Heat Stability at 190° C. (minutes) | Wet Heat Stability at 175° C. (minutes) |
|---|---|---|---|
| 43 | [structure: phosphite with two 3-methyl-5-t-octylphenoxy groups and one 3,5-di-t-butyl-4-(methoxycarbonylethyl)phenoxy group attached to P] | 110 | 140 |

It is apparent that the phosphites in accordance with the invention are far superior to the Controls.

EXAMPLES 44 TO 51

Ethylene-vinyl acetate copolymer resin compositions were prepared using phosphites of the invention and having the following formulation:

| Ingredient | Parts by Weight |
|---|---|
| Ethylene-vinyl acetate copolymer resin | 100 |
| Montan wax | 0.3 |
| 1,1,3-Tris(2'-methyl-4'-hydroxy-5'-t-butylphenyl)butane | 0.05 |
| Phosphite as shown in Table VI | 0.1 |

The stabilizers were blended with the resin on a two-roll mill, and sheeted off.

Samples of the sheets were heated in a Geer oven at 175° C. and the time in minutes to develop a noticeable discoloration and/or brittleness was noted.

Initial color was noted, as well as color at the time the noticeable discoloration had developed, and yellowness measured in a Hunter color difference meter, the difference in percent of yellowness being recorded.

The results are shown in Table VI.

TABLE VI

| Example No. | Phosphite | Heat Stability at 185° C. (minutes) | % of Initial Color |
|---|---|---|---|
| | None | 80 | 23 |
| Control | Tris(2,6-di-t-butyl-4-methylphenyl) phosphite | 95 | 18 |
| 44 | [structure: tetrameric phosphite with 3,5-di-t-butyl-4-hydroxyphenylthio linkages and 3,5-di-t-butyl-4-(methoxycarbonylethyl)phenoxy groups, ]₄C | 130 | 10 |
| 45 | [structure: phosphite with bis(3,5-di-t-butyl-4-hydroxyphenyl)methane bridge and 3,5-dimethyl-4-(methoxycarbonylethyl)phenoxy group] | 150 | 9 |

TABLE VI-continued

| Example No. | Phosphite | Heat Stability at 185° C. (minutes) | % of Initial Color |
|---|---|---|---|
| 46 | (structure: bis(3-methyl-5-cyclohexyl-2-hydroxyphenyl)methane linked via two O to P, with P—O—(2,6-di-tert-butyl-4-C₂H₄COOC₈H₁₇-phenyl)) | 130 | 10 |
| 47 | (structure: bis(3-methyl-5-cyclohexyl-2-hydroxyphenyl)methane linked via two O to P, with P—O—(2,6-di-tert-butyl-4-C₂H₄COOCH₃-phenyl)) | 150 | 10 |
| 48 | (structure: 2,2'-biphenyl diol with 3,3'-di-methyl and 5,5'-di-tert-butyl substituents, cyclic phosphite, P—O—(2,6-di-tert-butyl-4-C₂H₄COOC₈H₁₇-phenyl)) | 140 | 9 |
| 49 | (structure: 2,2'-biphenyl diol with 3,3'-di-methyl and 5,5'-di-t-C₈H₁₇ substituents, cyclic phosphite, P—O—(2,6-di-tert-butyl-4-C₂H₄COOCH₃-phenyl)) | 130 | 10 |
| 50 | (structure: 2,2'-biphenyl diol with 3,3'-di-methyl and 5,5'-di-tert-butyl substituents, cyclic phosphite, P—O—(2,6-di-tert-butyl-4-C₂H₄COOCH₃-phenyl)) | 140 | 10 |

TABLE VI-continued

| Example No. | Phosphite | Heat Stability at 185° C. (minutes) | % of Initial Color |
|---|---|---|---|
| 51 | 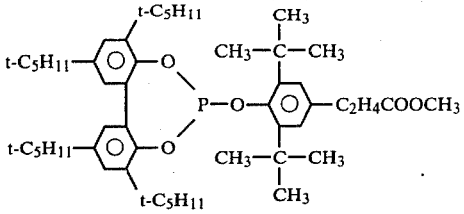 | 150 | 10 |

It is apparent from the data that the phosphites of the invention are far superior to the Control

EXAMPLES 52 TO 59

Polyester resin compositions were prepared using phosphites of the invention and having the formulation:

| Ingredient | Parts by Weight |
|---|---|
| Polybutylene terephalate | 100 |
| 1,3,5-Tris(3',5'-di-t-butyl-4'-hydroxybenzyl)-2,4,6-trimethylbenzene | 0.2 |
| Phosphite as shown in Table VII | 0.2 |

Compositions according to the above formulation were blended and injection molded at 270° C. to prepare test pieces. Tensile strength of the pieces before and after heat ageing at 150° C. for 240 hours was determined and the results are reported as the percent of tensile strength retained.

The results are shown in Table VII.

TABLE VII

| | Phosphite | % Tensile Strength Retained |
|---|---|---|
| Control | | |
| | None | 55 |
| 1 | Tris(2,4-di-t-butyl-octylphenyl) phosphite | 72 |
| 2 | Tris(2-t-butylphenyl) phosphite | 64 |
| Example No. | | |
| 52 | 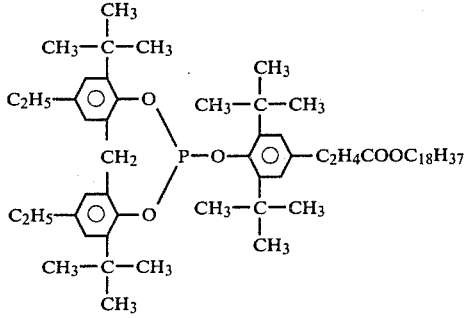 | 94 |
| 53 | 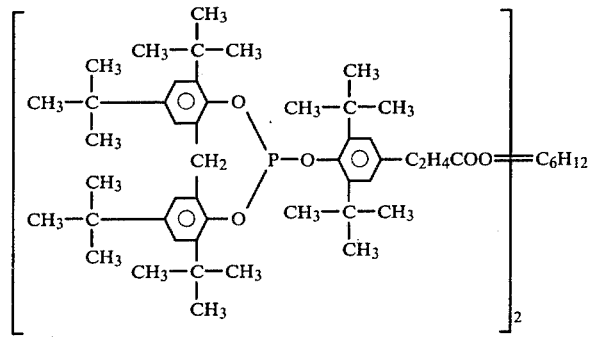 | 88 |

TABLE VII-continued
| | Phosphite | % Tensile Strength Retained |
|---|---|---|
| 54 | 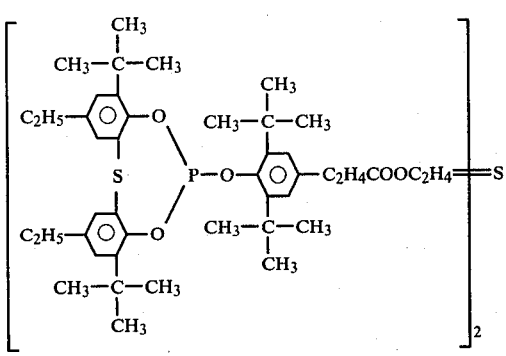 | 88 |
| 55 | 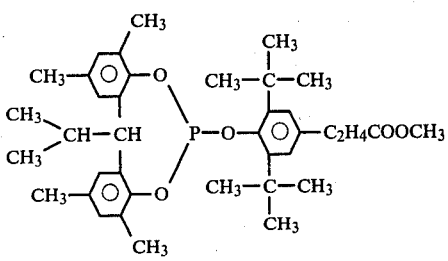 | 92 |
| 56 | 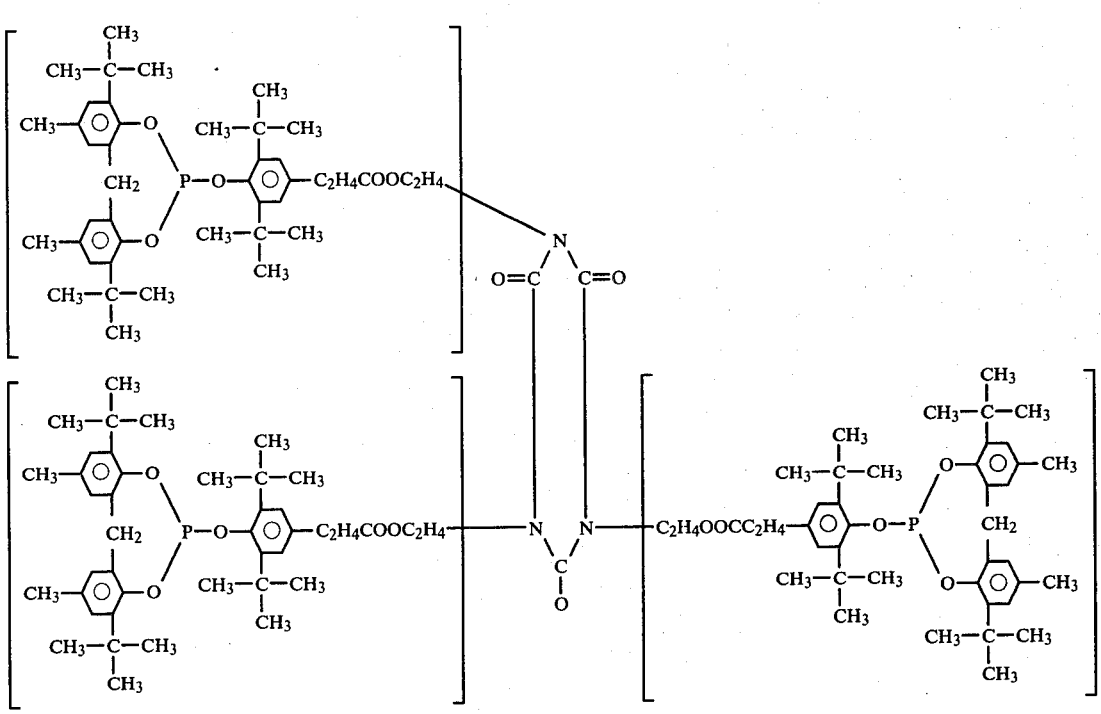 | 90 |

TABLE VII-continued

| | Phosphite | % Tensile Strength Retained |
|---|---|---|
| 57 | [Structure: phosphite with two 3,5-di-t-butyl-methylphenyl groups linked via O to P-O-(2,6-di-t-butylphenyl)-C₂H₄COOC₈H₁₇] | 88 |
| 58 | [Structure: phosphite with two 3-methyl-5-t-octylphenyl groups linked via O to P-O-(2,6-di-t-butylphenyl)-C₂H₄COOCH₃] | 90 |
| 59 | [Structure: phosphite with two 3-methyl-5-t-butyl groups (each with additional t-butyl) linked via O to P-O-(2,6-di-t-butylphenyl)-C₂H₄COOCH₃] | 80 |

The superiority to the Controls of the phosphites of the invention is evident from these results.

EXAMPLES 60 TO 64

Cis-1,4-polyisoprene polymer (m.w. 680,000) 100 g and the phosphite shown in Table VIII 0.5 g were dissolved in 250 ml of isooctane and then the isooctane was evaporated.

The polyisoprene compositions were heated in a Geer oven at 100° C. for three hours, and the color of the compositions was observed, and their inherent viscosity (in toluene) was measured before and after heating.

The results are shown in Table VIII.

TABLE VIII

| Example No. | Phosphite | Color | Inherent Viscosity Original | Inherent Viscosity after heating |
|---|---|---|---|---|
| Control | None | Brown | 3.8 | |
| | Tris(2,4-di-t-butylphenyl)phosphite | Pale brown | 4.6 | 4.0 |
| 60 | [Structure: phosphite with two 3-t-butyl-5-ethyl phenyl groups joined by CH₂ bridge, linked via O to P-O-(2,6-di-t-butylphenyl)-C₂H₄COOC₁₈H₃₇] | Pale Yellow | 4.8 | |

TABLE VIII-continued

| Example No. | Phosphite | Color | Inherent Viscosity Original | Inherent Viscosity after heating |
|---|---|---|---|---|
| 61 | 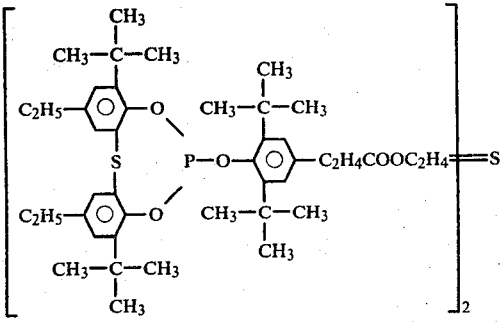 | Colorless | 4.7 | |
| 62 | 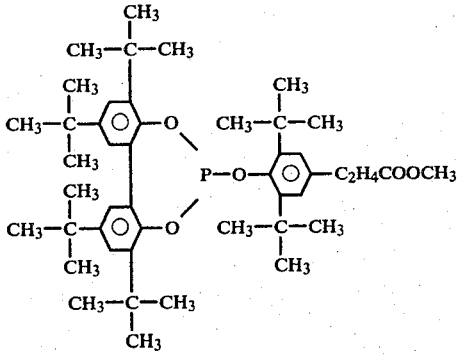 | Colorless | 4.7 | |
| 63 | 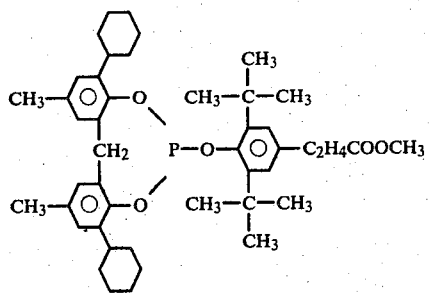 | Colorless | 4.7 | |
| 64 | 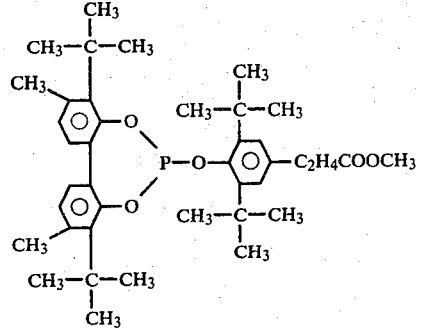 | Pale yellow | 4.8 | |

EXAMPLES 65 to 72

Polycarbonate resin compositions were prepared having the following formulation:

| Ingredient | Parts by Weight |
|---|---|
| Polycarbonate | 100 |
| Phosphite as shown in TABLE IX | 0.1 |

The ingredients were mixed and compression molded at 260° C. to prepare sheets 1 mm thick. Heat stability was evaluated by heating the sheets in a Geer oven at 230° C. for thirty minutes, and then observing the color of the sheets.

The results are shown in Table IX.

TABLE IX
| | Phosphite | Color of Test piece |
|---|---|---|
| Control | | |
| | None | Dark brown |
| | Tris(nonylphenyl) phosphite | Brown |
| Example No. | | |
| 65 | 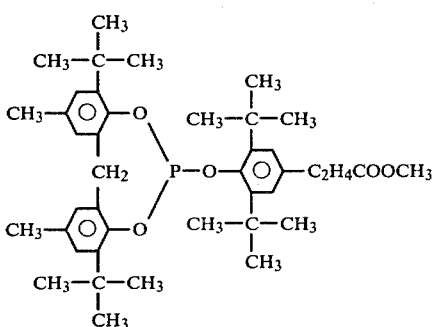 | Pale yellow |
| 66 | 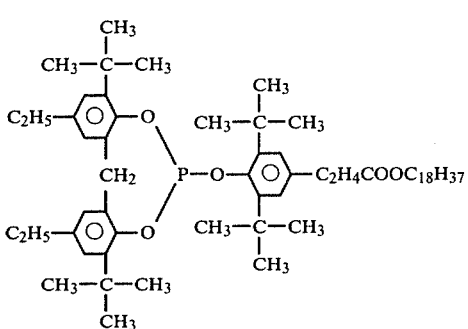 | Colorless |
| 67 | 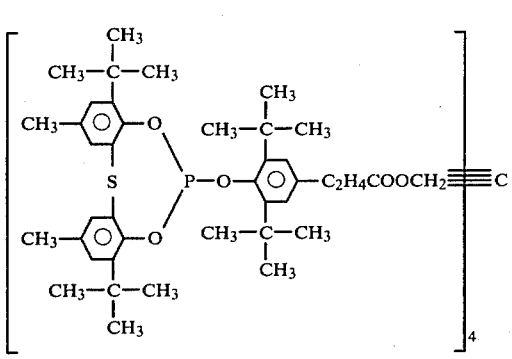 | Colorless |
| 68 | 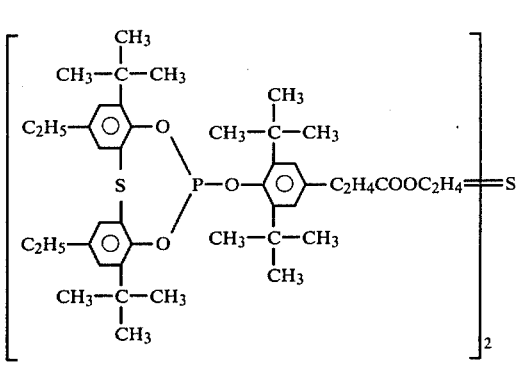 | Colorless |

TABLE IX-continued

| | Phosphite | Color of Test piece |
|---|---|---|
| 69 | 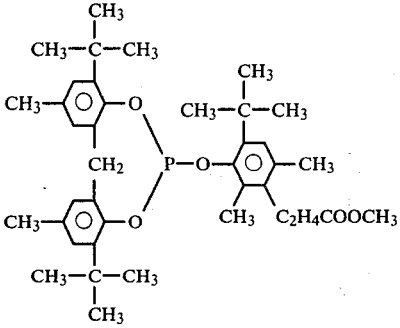 | Pale Yellow |
| 70 | 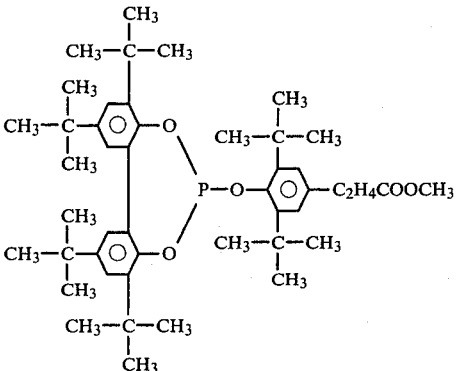 | Pale Yellow |
| 71 | 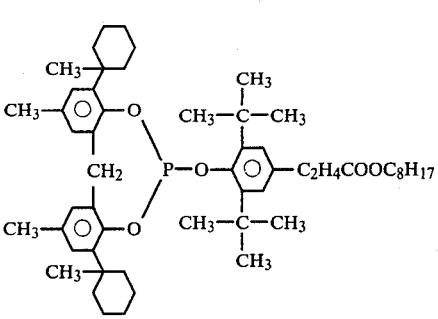 | Pale Yellow |
| 72 | 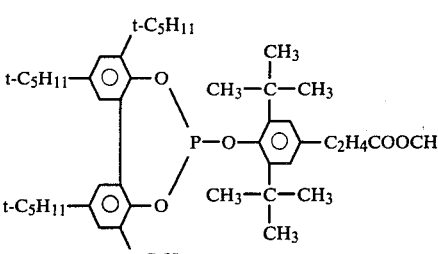 | Pale Yellow |

The phosphites of the invention are clearly more effective heat stabilizers than the Control.

Having regard to the foregoing disclosure, the following is claimed as the inventive and patentable embodiments thereof:

1. Hindered bis-phenol phenyl phosphites having the structure:

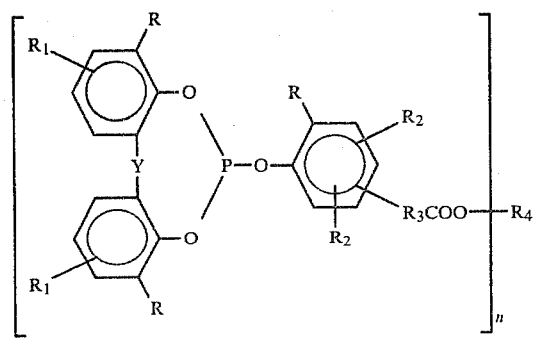

wherein:
R is selected from the group consisting of alkyl having from one up to about eighteen carbon atoms; and cycloalkyl having from three up to about twelve carbon atoms, alkaryl and aryl having from six to about eighteen carbon atoms;

$R_1$ and $R_2$ are each selected from the group consisting of hydrogen and alkyl having from one to about eighteen carbon atoms; cycloalkyl having from three up to about twelve carbon atoms; alkaryl and aryl having from six to about eighteen carbon atoms;

$R_3$ is alkylene having from one to about six carbon atoms;

$R_4$ is selected from the group consisting of monovalent alkyl, cycloalkyl and aralkyl and polyvalent alkylene, cycloalkylene and aralkylene and monovalent and polyvalent 2-ethylene isocyanurate having from one to about eighteen carbon atoms, and from none to three hydroxyl groups;

Y is selected from the group consisting of a direct carbon to carbon bond, thio sulfur —S—; oxy oxygen —O—; alkylidene having from one to about six carbon atoms; and cycloalkylidene having from four to about eight carbon atoms; and n is, 2, 3 or 4, according to the valence of $R_4$.

2. A hindered bis-phenol phenyl phosphite according to claim 1 in which R is a bulky iso, secondary or tertiary alkyl having from three to about ten carbon atoms; or cycloalkyl having six to twelve carbon atoms.

3. A hindered bis-phenol phenyl phosphite according to claim 1 in which $R_1$ and $R_2$ are in a position ortho to a phenolic hydroxyl or phenoxy group.

4. A hindered bis-phenol phenyl phosphite according to claim 1 in which n is 2.

5. A hindered bis-phenol phenyl phosphite according to claim 1 in which n is 3.

6. A hindered bis-phenol phenyl phosphite according to claim 1 in which n is 4.

7. A hindered bis-phenol phenyl phosphite according to claim 1 in which R is tertiary butyl.

8. A hindered bis-phenol phenyl phosphite according to claim 1 in which Y is thio sulfur —S—.

9. A hindered bis-phenol phenyl phosphite according to claim 1 in which Y is alkylidene.

10. A hindered bis-phenol phenyl phosphite according to claim 1 in which Y is cycloalkylidene.

11. A hindered bis-phenol phenyl phosphite according to claim 1 in which Y is oxy oxygen —O—.

12. A hindered bis-phenol phenyl phosphite according to claim 1 in which R is alkyl.

13. A hindered bis-phenol phenyl phosphite according to claim 1 in which R is aryl.

14. A hindered bis-phenol phenyl phoshite according to claim 1 in which R is alkaryl.

15. A hindered bis-phenol phenyl phoshite according to claim 1 having the formula:

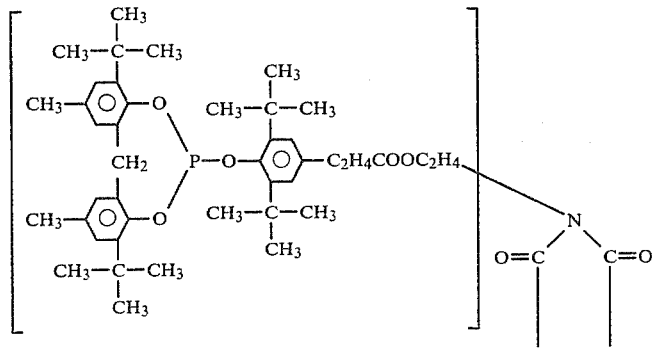

16. A hindered bis-phenol phenyl phosphite according to claim 1 having the formula:

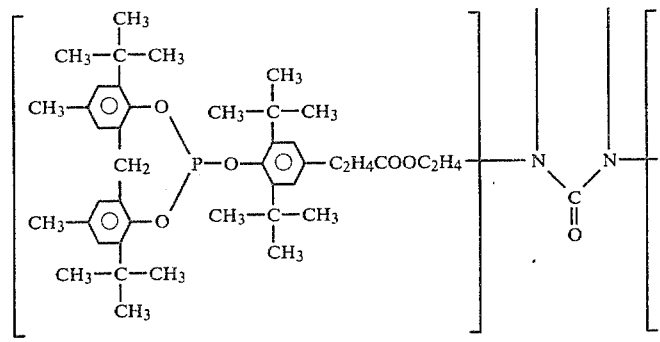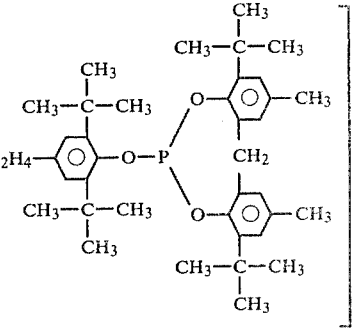

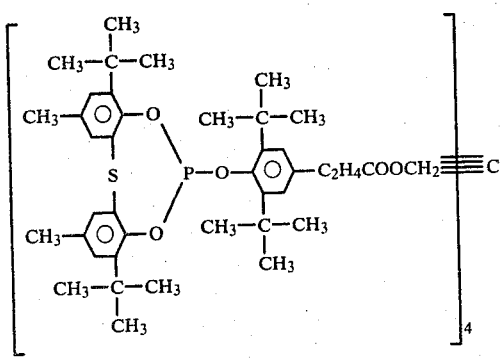

17. A polyvinyl chloride resin composition having improved resistance to deterioration when heated at 350° F., comprising a polyvinyl chloride resin formed at least in part of the recurring group

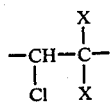

and having a chlorine content in excess of 40%, where X is either hydrogen or chlorine; and a phosphite in accordance with claim 1.

18. A polyvinyl chloride resin composition in accordance with claim 17, in which the polyvinyl chloride resin is polyvinyl chloride homopolymer.

19. A polyvinyl chloride resin composition in accordance with claim 17, in which the polyvinyl chloride resin is a copolymer of vinyl chloride and vinyl acetate.

20. An olefin polymer composition having improved resistance to deterioration comprising an olefin polymer selected from the group consisting of polymers of alpha-olefins having from two to six carbon atoms and polystyrene, and a phosphite in accordance with claim 1.

21. An olefin polymer composition in accordance with claim 20 wherein the polyolefin is polypropylene.

22. An olefin polymer composition in accordance with claim 24 wherein the polyolefin is polyethylene.

23. An acrylonitrile-butadiene-styrene terpolymer having improved resistance to deterioration comprising acrylonitrile-butadiene-styrene terpolymer and a phosphite in accordance with claim 1.

24. An ethylene-vinyl acetate copolymer composition having improved resistance to deterioration comprising ethylene-vinyl acetate copolymer and a phosphite in accordance with claim 1.

25. A polycarbonate resin composition having improved resistance to deterioration comprising a polycarbonate resin and a phosphite in accordance with claim 1.

26. A polyester polymer composition having improved resistance to deterioration comprising an ester resin and a phosphite in accordance with claim 1.

* * * * *

UNITED STATES PATENT AND TRADEMARK OFFICE
CERTIFICATE OF CORRECTION

PATENT NO. : 4,362,830
DATED : December 7, 1982
INVENTOR(S) : Motonobu Minagawa et al It is certified that error appears in the above-identified patent and that said Letters Patent are hereby corrected as shown below:

Column 5, line 25 : "$-PR'_2$" should be -- $-PR_2'$ --

Column 6, line 20 :

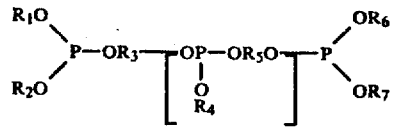

should be

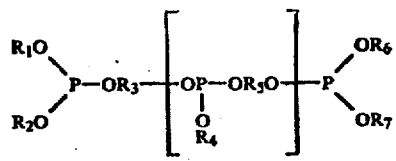

Column 12, line 7 : "-6t" should be --6-t- --.

Column 13, Formula 10 : ⬡ should be ⬡(O)

Signed and Sealed this

Twenty-fourth Day of September 1985

[SEAL]

Attest:

DONALD J. QUIGG

Attesting Officer

Commissioner of Patents and Trademarks—Designate

UNITED STATES PATENT AND TRADEMARK OFFICE
CERTIFICATE OF CORRECTION

PATENT NO. : 4,362,830
DATED : December 7, 1982
INVENTOR(S) : Motonobu Minagawa et al It is certified that error appears in the above-identified patent and that said Letters Patent are hereby corrected as shown below:

Column 63 :  Claim 15, that portion of the formula reading

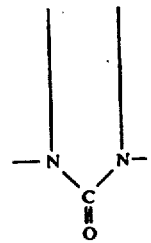

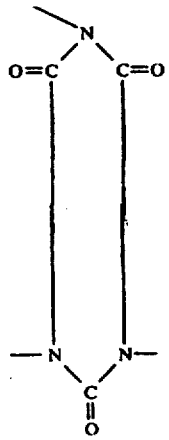

should be